(12) United States Patent
Joly et al.

(10) Patent No.: US 11,365,362 B2
(45) Date of Patent: Jun. 21, 2022

(54) DEVICE AND PROCESS FOR THE PRODUCTION OF AROMATICS FROM A BIOMASS PYROLYSIS GAS

(71) Applicant: IFP Energies nouvelles, Rueil-Malmaison (FR)

(72) Inventors: Jean-Francois Joly, Rueil-Malmaison (FR); Frederic Feugnet, Rueil-Malmaison (FR)

(73) Assignee: IFP Energies nouvelles, Rueil-Malmaison (FR)

(*) Notice: Subject to any disclaimer, the term of this patent is extended or adjusted under 35 U.S.C. 154(b) by 0 days.

(21) Appl. No.: 17/373,030

(22) Filed: Jul. 12, 2021

(65) Prior Publication Data

US 2022/0041943 A1 Feb. 10, 2022

(30) Foreign Application Priority Data

Jul. 27, 2020 (FR) .................................... 2007914

(51) Int. Cl.
*C10G 69/12* (2006.01)
*C10B 53/02* (2006.01)
(Continued)

(52) U.S. Cl.
CPC ............ *C10G 69/123* (2013.01); *C10B 53/02* (2013.01); *C10B 57/06* (2013.01); *C10G 69/126* (2013.01);
(Continued)

(58) Field of Classification Search
CPC ........... C07C 7/04; C07C 15/04; C07C 15/06; C07C 7/10; C07C 15/08; C10G 69/123; C10G 69/126; C10G 2300/1011; C10G 2300/1022; C10G 2300/4006; C10G 2300/4012; C10G 2300/4018; C10G 2400/30; C10G 1/002; C10G 1/02; C10G 1/086; C10G 2/32; C10B 53/02; C10B 57/06; C10J 3/64; C10J 2300/0903;
(Continued)

(56) References Cited

U.S. PATENT DOCUMENTS

| 4,678,860 A | 7/1987 | Kuester |
| 9,422,492 B2* | 8/2016 | Boissonnet ............... C10K 3/06 |
| 2007/0100003 A1* | 5/2007 | Holley ...................... C10K 1/04 |
| | | 518/703 |
| 2008/0047872 A1 | 2/2008 | Iaccino et al. |
| 2009/0286889 A1* | 11/2009 | Fiato ................... C07C 29/1518 |
| | | 518/700 |

(Continued)

OTHER PUBLICATIONS

Preliminary Search Report in French Patent Application No. 2007914 dated Apr. 13, 2021.

*Primary Examiner* — Ali Z Fadhel
(74) *Attorney, Agent, or Firm* — Fitch, Even, Tabin & Flannery, LLP (57) ABSTRACT

A device and process for the conversion of aromatic compounds, includes/uses: a unit for the separation of the xylenes suitable for treating a cut comprising xylenes and ethylbenzene and producing an extract comprising para-xylene and a raffinate; an isomerization unit suitable for treating the raffinate and producing an isomerate enriched in para-xylene which is sent to a fractionation train; a pyrolysis unit suitable for treating biomass, producing a pyrolysis effluent feeding, at least partially, the feedstock, and producing a pyrolysis gas comprising CO and $H_2$; a Fischer-Tropsch synthesis reaction section suitable for treating, at least in part, the pyrolysis gas, producing a synthesis effluent sent, at least in part, to the pyrolysis unit.

15 Claims, 1 Drawing Sheet

(51) Int. Cl.
*C10B 57/06* (2006.01)
*C10J 3/64* (2006.01)

(52) U.S. Cl.
CPC ......... *C10J 3/64* (2013.01); *C10G 2300/1011* (2013.01); *C10G 2300/1022* (2013.01); *C10G 2300/4006* (2013.01); *C10G 2300/4012* (2013.01); *C10G 2300/4018* (2013.01); *C10G 2400/30* (2013.01); *C10J 2300/0903* (2013.01); *C10J 2300/0986* (2013.01); *C10J 2300/1207* (2013.01); *C10J 2300/1659* (2013.01)

(58) Field of Classification Search
CPC ........ C10J 2300/0986; C10J 2300/1207; C10J 2300/1659; C10J 2300/1807; C10J 3/00
See application file for complete search history.

(56) References Cited

U.S. PATENT DOCUMENTS

| | | | |
|---|---|---|---|
| 2011/0275869 A1* | 11/2011 | Prochazka | C10G 3/00 585/242 |
| 2014/0262965 A1* | 9/2014 | Bauman | C10G 1/08 208/400 |
| 2016/0272665 A1* | 9/2016 | Delgass | C07C 41/18 |
| 2016/0304788 A1 | 10/2016 | Sorensen et al. | |
| 2017/0137350 A1 | 5/2017 | Weiss et al. | |
| 2020/0165527 A1 | 5/2020 | Digne et al. | |
| 2021/0292666 A1* | 9/2021 | Greager | C10G 47/00 |
| 2021/0317375 A1* | 10/2021 | Greager | C10K 1/005 |
| 2021/0355392 A1* | 11/2021 | Greager | C10K 1/005 |

\* cited by examiner

DEVICE AND PROCESS FOR THE PRODUCTION OF AROMATICS FROM A BIOMASS PYROLYSIS GAS

CROSS-REFERENCE TO RELATED APPLICATIONS

This application claims priority from French Patent Application No. 20/07.914 filed Jul. 27, 2020, which is hereby incorporated herein by reference in its entirety for all purposes.

TECHNICAL FIELD

The invention relates to the production of aromatics for the petrochemical industry (benzene, toluene, para-xylene, ortho-xylene). More particularly, the object of the invention is to be able to increase the production of aromatics produced by a process for the pyrolysis of biomass.

The aromatic complex (or device for the conversion of aromatic compounds) is fed with feedstocks composed predominantly of six to ten carbon atoms or more, referred to as C6 to C10+ feedstocks. Various sources of aromatic compounds can be introduced into an aromatic complex, the most widespread source being the process for the catalytic reforming of naphtha. Mixtures of aromatic compounds obtained by a process for the conversion of lignocellulosic biomass can also, after a purification treatment, be introduced into an aromatic complex. The process for the catalytic pyrolysis of lignocellulosic biomass can, for example, be considered as a source of aromatics.

Within an aromatic complex, whatever the source of aromatics, benzene and alkylaromatics (e.g. toluene, para-xylene, ortho-xylene) are extracted therefrom and then converted into desired intermediates. The products of interest are aromatics with 0 (benzene), 1 (toluene) or 2 (xylenes) methyl groups, and in particular, within the xylenes, para-xylene, having the greatest market value.

PRIOR ART

To date, aromatic complexes make it possible to produce benzene, optionally toluene, and xylenes (often para-xylene, sometimes ortho-xylene). An aromatic complex generally possesses at least one catalytic unit exhibiting at least one of the following functions:
  the isomerization of aromatic compounds having eight carbon atoms, denoted A8 compounds, making it possible to convert ortho-xylene, meta-xylene and ethylbenzene into para-xylene;
  transalkylation, making it possible to produce xylenes from a mixture of toluene (and optionally of benzene) and of A9+ compounds, such as trimethylbenzenes and tetramethylbenzenes; and
  the disproportionation of toluene, which makes it possible to produce benzene and xylenes.

The aromatic loop makes it possible to produce high-purity para-xylene by separation by adsorption or by crystallization, an operation which is well known from the prior art. This "C8 aromatic loop" includes a stage of removal of the heavy compounds (i.e., C9+ compounds) in a distillation column known as "xylenes column". The top stream from this column, which contains the C8 aromatic isomers (i.e., A8 isomers), is subsequently sent to the process for separation of the para-xylene which is, very generally, a process for separation by simulated moving bed (SMB) adsorption, to produce an extract and a raffinate, or a crystallization process, in which a para-xylene fraction is isolated from the remainder of the constituents of the mixture in the form of crystals.

The extract, which contains the para-xylene, is subsequently distilled in order to obtain high-purity para-xylene. The raffinate, which is rich in meta-xylene, ortho-xylene and ethylbenzene, is treated in a catalytic isomerization unit which restores a mixture of C8 aromatics in which the proportion of the xylenes (ortho-, meta-, para-xylenes) is virtually at thermodynamic equilibrium and the amount of ethylbenzene is reduced. This mixture is again sent to the "xylenes column" with the fresh feedstock.

All the industrial processes for the isomerization of C8 aromatics make it possible to isomerize xylenes. The conversion of ethylbenzene depends, on the other hand, on the type of process and of catalyst which are chosen. This is because petrochemical complexes utilize an "isomerizing" isomerization unit (i.e. isomerization of ethylbenzene to give a mixture of C8 aromatics) or a "dealkylating" isomerization unit (i.e., dealkylation of ethylbenzene to give benzene), in order to favour the production (at the outlet of the aromatic loop) respectively either of para-xylene alone or of benzene and para-xylene.

The choice of an "isomerizing" isomerization makes it possible, as indicated above, to maximize the production of para-xylene, which is the compound having the highest added value at the outlet of the aromatic complex. The combination within an aromatic complex of an "isomerizing" isomerization and of a liquid-phase isomerization, such as described, for example, in the patents U.S. Pat. Nos. 8,697,929, 7,371,913, 4,962,258, 6,180,550, 7,915,471, 10,035,739 and 10,029,958, makes it possible in particular to maximize the amount of para-xylene produced while having a reduced loss of aromatic rings, in comparison with an aromatic complex according to the prior art.

SUMMARY OF THE INVENTION

In the context described above, a first object of the present description is to overcome the problems of the prior art and to provide a device and a process for the production of aromatics for the petrochemical industry making it possible, when the aromatic compounds are produced by pyrolysis of biomass, to convert the CO, a byproduct of the pyrolysis section, into additional paraffins and aromatic compounds.

The invention is based on the conversion of the carbon monoxide, i.e. CO, into paraffins and into aromatic compounds which are introduced into the aromatic complex, and on the provision of one or more units making it possible to convert the CO into a mixture of liquid hydrocarbons predominantly consisting of olefins, this mixture of hydrocarbons being recycled to the section for pyrolysis of biomass in order to be converted therein in particular into aromatic compounds. Specifically, the object of the present invention can amount to adding a catalytic Fischer-Tropsch unit, preferably operated at high temperature and/or in the presence of an iron catalyst, this catalytic unit making it possible to convert synthesis gas $CO+H_2$ into a mixture of liquid hydrocarbons. At least a part and preferably all of the effluent exiting from the Fischer-Tropsch reaction zone is recycled at the inlet of the section for pyrolysis of biomass.

According to a first aspect, the abovementioned objects, and also other advantages, are obtained by a device for the conversion of a feedstock of aromatic compounds, comprising:

a fractionation train suitable for extracting at least one cut comprising benzene, one cut comprising toluene and one cut comprising xylenes and ethylbenzene from the feedstock;

a unit for the separation of the xylenes suitable for treating the cut comprising xylenes and ethylbenzene and producing an extract comprising para-xylene and a raffinate comprising ortho-xylene, meta-xylene and ethylbenzene;

an isomerization unit suitable for treating the raffinate and producing an isomerate enriched in para-xylene which is sent to the fractionation train;

a pyrolysis unit suitable for treating biomass, producing at least one pyrolysis effluent comprising hydrocarbon compounds of 6 to 10 carbon atoms feeding at least partially the feedstock, and producing a pyrolysis gas comprising at least CO and $H_2$;

a Fischer-Tropsch synthesis reaction section suitable for treating the pyrolysis gas at least in part, producing a synthesis effluent comprising hydrocarbon compounds of 3 to 22 carbon atoms, and sending the synthesis effluent, at least in part, to the pyrolysis unit.

According to one or more embodiments, the pyrolysis gas additionally comprises $CO_2$ at the outlet of the pyrolysis unit.

According to one or more embodiments, the device additionally comprises a unit for the separation of $CO_2$ positioned between the pyrolysis unit and the Fischer-Tropsch reaction section, and suitable for extracting, at least in part, $CO_2$ from the pyrolysis gas.

According to one or more embodiments, the fractionation train is suitable for extracting a C9-C10 monoaromatics cut from the feedstock.

According to one or more embodiments, the device additionally comprises a transalkylation unit suitable for treating the C9-C10 monoaromatics cut with the toluene-comprising cut and producing xylenes which are sent to the fractionation train.

According to one or more embodiments, the device additionally comprises a selective hydrogenolysis unit is suitable for:
treating the C9-C10 monoaromatics cut; and
producing a hydrogenolysis effluent enriched in methyl-substituted aromatic compounds which is sent to the transalkylation unit.

According to one or more embodiments, the Fischer-Tropsch synthesis reaction section is suitable for recycling the synthesis effluent in its entirety in the pyrolysis unit.

According to a second aspect, the abovementioned objects, and also other advantages, are obtained by a process for the conversion of a feedstock of aromatic compounds, comprising the following stages:

fractionating the feedstock in a fractionation train in order to extract at least one benzene-comprising cut, one toluene-comprising cut and one cut comprising xylenes and ethylbenzene;

separating the cut comprising xylenes and ethylbenzene in a unit for the separation of the xylenes and producing an extract comprising para-xylene and a raffinate comprising ortho-xylene, meta-xylene and ethylbenzene;

isomerizing the raffinate in an isomerization unit and producing an isomerate enriched in para-xylene;

sending the isomerate enriched in para-xylene to the fractionation train;

treating biomass in a pyrolysis unit in order to produce at least one pyrolysis effluent comprising hydrocarbon compounds of 6 to 10 carbon atoms feeding, at least partially, the feedstock and to produce a pyrolysis gas comprising at least CO and $H_2$;

treating, at least in part, the pyrolysis gas in a Fischer-Tropsch synthesis reaction section in order to produce a synthesis effluent comprising hydrocarbon compounds of 3 to 22 carbon atoms; and sending the synthesis effluent, at least in part, to the pyrolysis unit.

According to one or more embodiments, the pyrolysis unit comprises at least one reactor used under the following operating conditions:

presence of a catalyst, preferably a zeolite catalyst, preferably a zeolite catalyst comprising at least one zeolite chosen from ZSM-5, ferrierite, zeolite beta, zeolite Y, mordenite, ZSM-23, ZSM-57, EU-1 or ZSM-11, preferably a catalyst comprising only a zeolite of ZSM-5 type; the zeolite used in the catalyst can advantageously be doped with a metal chosen from iron, gallium, zinc and lanthanum;

a temperature of between 400° C. and 1000° C., preferably between 400° C. and 650° C., in a preferred way between 450° C. and 600° C. and in a very preferred way between 450° C. and 590° C.;

an absolute pressure of between 0.1 and 0.5 MPa;

an HSV of between 0.01 and 10 $h^{-1}$, preferably between 0.01 and 5 $h^{-1}$, in a preferred way between 0.1 and 3 $h^{-1}$ and in a very preferred way between 0.1 and 3 $h^{-1}$ (the HSV is the ratio of the flow rate by volume of feedstock to the volume of catalyst used).

According to one or more embodiments, the Fischer-Tropsch synthesis reaction section is used under the following operating conditions:

temperature of between 250° C. and 400° C., preferably of between 300° C. and 350° C. and very preferably still of between 300° C. and 340° C.;

pressure of between 1 and 5 MPa, preferably of between 1.5 and 4 MPa and very preferably of between 2 and 3 MPa (e.g. at 2.5 MPa±2);

catalyst comprising iron as active phase;

flow rate by volume of the synthesis effluent of between 400° C. and preferably between 0.5 and 1.5l/$g_{cata}$/h.

According to one or more embodiments, the isomerization unit comprises a gas-phase isomerization zone and/or a liquid-phase isomerization zone, in which the gas-phase isomerization zone is used under the following operating conditions:

temperature of greater than 300° C.;

pressure of less than 4.0 MPa;

hourly space velocity of less than 10 $h^{-1}$;

hydrogen to hydrocarbon molar ratio of less than 10;

in the presence of a catalyst comprising at least one zeolite exhibiting channels, the opening of which is defined by a ring having 10 or 12 oxygen atoms, and at least one metal from group VIII with a content of between 0.1% and 0.3% by weight, limits included, with respect to the total weight of the catalyst, and in which the liquid-phase isomerization zone is used under the following operating conditions:

temperature of less than 300° C.;

pressure of less than 4 MPa;

hourly space velocity of less than 10 $h^{-1}$;

in the presence of a catalyst comprising at least one zeolite exhibiting channels, the opening of which is defined by a ring having 10 or 12 oxygen atoms.

According to one or more embodiments, the transalkylation unit comprises at least one first transalkylation reactor used under the following operating conditions:

temperature of between 200° C. and 600° C.;
pressure of between 2 and 10 MPa;
WWH of between 0.5 and 5 h$^{-1}$.

According to one or more embodiments, the pyrolysis gas additionally comprises $CO_2$ at the outlet of the pyrolysis unit.

According to one or more embodiments, the process comprises the following stage:
extracting, at least in part, the $CO_2$ from the pyrolysis gas in a unit for the separation of $CO_2$ positioned between the pyrolysis unit and the Fischer-Tropsch reaction section.

According to one or more embodiments, the synthesis effluent is recycled in its entirety in the pyrolysis unit.

Embodiments according to the first aspect and the second aspect, and also other characteristics and advantages of the devices and processes according to the abovementioned aspects, will become apparent on reading the description which will follow, which is given solely by way of illustration and without limitation, and with reference to the following drawing.

DESCRIPTION OF THE EMBODIMENTS

Figure 1:
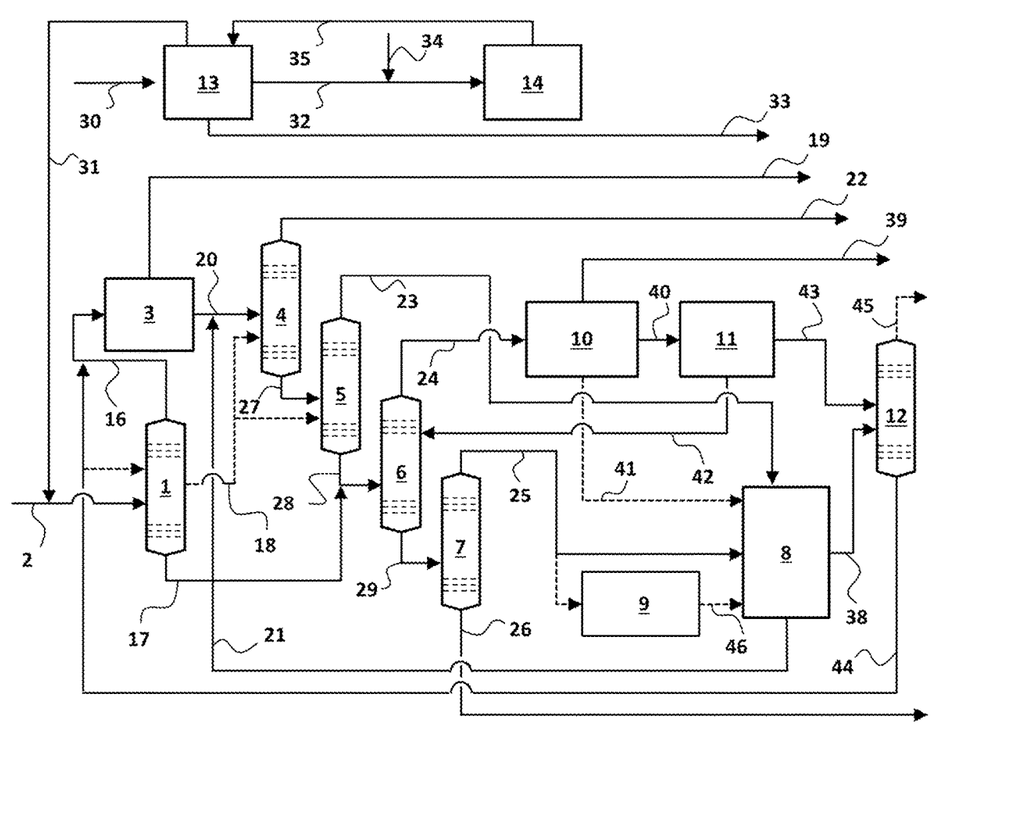
The FIGURE represents a diagrammatic view of a process according to the present invention which makes it possible to increase the production of aromatic compounds.

Embodiments of the device according to the first aspect and of the process according to the second aspect will now be described in detail. In the following detailed description, numerous specific details are explained in order to provide a deeper understanding of the device. However, it will be apparent to a person skilled in the art that the device can be implemented without these specific details. In other cases, well-known characteristics have not been described in detail in order to avoid unnecessarily complicating the description.

In the present patent application, the term "to comprise" is synonymous with (means the same thing as) "to include" and "to contain", and is inclusive or open and does not exclude other elements which are not stated. It is understood that the term "to comprise" includes the exclusive and closed term "to consist". Moreover, in the present description, an effluent comprising essentially or solely compounds A corresponds to an effluent comprising at least 80% or 90% by weight, preferably at least 95% by weight, very preferably at least 99% by weight, of compounds A.

The present invention can be defined as a device and a process comprising a sequence of unit operations making it possible to produce aromatic compounds, such as para-xylene and benzene.

The device and the process according to the invention are characterized in that they comprise and use the catalytic units and the separation units which are known to a person skilled in the art for producing benzene and para-xylene, which units are commonly encountered in aromatic complexes.

One of the characteristics of the present invention consists of the use of CO, a byproduct of a unit for the pyrolysis of biomass, for increasing the production of aromatic compounds.

Surprisingly, the combination of the reaction section for the conversion of a mixture comprising CO and $H_2$ in a Fischer-Tropsch unit and the recycle of all of the effluent from said reaction section at the inlet of the pyrolysis unit makes it possible to significantly increase the amount of aromatics produced by pyrolysis of biomass.

With reference to the FIGURE, according to one or more embodiments, the device for conversion of aromatic compounds comprises:
an optional feedstock separation unit 1 for separating an incoming feedstock 2 of the aromatic complex into a hydrocarbon cut having 7 or less carbon atoms (C7-) and an aromatic cut having 8 or more carbon atoms (A8+);
an optional unit for extraction of the aromatics 3 between the feedstock separation unit 1 and a fractionation train 4-7 in order to separate the aliphatic compounds from the benzene and the toluene of the C7- cut of the feedstock of the complex;
the fractionation train 4-7 downstream of the optional unit for extraction of the aromatics 3, making it possible to extract the benzene, the toluene and the xylenes from the other aromatics;
an optional transalkylation unit 8 which converts toluene (and optionally benzene) and methylalkylbenzenes, such as trimethylbenzenes, into xylenes—advantageously, this unit can also treat tetramethylbenzenes;
an optional selective hydrogenolysis unit 9 suitable for treating a cut comprising aromatic compounds having 9 and 10 carbon atoms and producing a hydrogenolysis effluent enriched in methyl-substituted aromatic compounds;
an optional separation unit (not shown) for separating the hydrogenolysis effluent positioned (e.g., directly) downstream of the selective hydrogenolysis unit 9, for producing a plurality of liquid effluent cuts;
a unit for the separation of the xylenes 10 (e.g., of the type of crystallization or simulated moving bed using a molecular sieve and a desorbent, such as toluene) making it possible to isolate the para-xylene from the xylenes and the ethylbenzene;
a unit for isomerization 11 of the raffinate obtained as effluent from the unit for the separation of the xylenes 10, in order to convert in particular the ortho-xylene, the meta-xylene and the ethylbenzene into para-xylene;
an optional stabilization column 12 which makes it possible in particular to remove the more volatile entities (e.g., C5- entities) from the aromatic complex, in particular effluents from the transalkylation unit 8 and/or the isomerization unit 11;
a pyrolysis unit 13, preferably a catalytic pyrolysis unit, for treating biomass 30, producing at least one pyrolysis effluent 31 feeding, at least partially, the incoming feedstock 2 of the aromatic complex, a pyrolysis gas 32 comprising at least CO and $H_2$, and a line of middle distillates 33 which, after an optional hydrotreating and/or hydrocracking stage, can be upgraded in the form of jet fuel, gas oil or marine fuel oil;
an optional unit of the separation of $CO_2$ (not represented) positioned between the pyrolysis unit 13 and a Fischer-Tropsch synthesis reaction section 14 for reducing the $CO_2$ content of the pyrolysis gas 32;
an optional backup line 34 for providing a contribution of $H_2$ and adjusting the $H_2/CO$ ratio of the pyrolysis gas 32;
an optional hydrotreating unit (not represented) suitable for hydrotreating the pyrolysis effluent 31, being preferably suitable for reducing the content of oxygen-based compounds of the pyrolysis effluent 31, and being preferably positioned upstream of the optional feedstock separation unit 1, such as upstream of the incoming feedstock line 2; and a Fischer-Tropsch synthesis reaction section 14 for converting the pyrolysis gas 32 and sending at least a part of the synthesis effluent 35 to the pyrolysis unit 13.

With reference to the FIGURE, the feedstock separating unit 1 treats the incoming feedstock 2 of the aromatic complex in order to separate a top cut 16 comprising (e.g., essentially) compounds having 7 or less carbon atoms (C7-), containing in particular benzene and toluene, and a bottom cut 17 comprising (e.g., essentially) aromatics having 8 or more carbon atoms (A8+) which is sent to the xylene column 6. According to one or more embodiments, the feedstock separation unit 1 also separates a first toluene cut 18 comprising at least 90% by weight, preferably at least 95% by weight, very preferably at least 99% by weight, of toluene, with respect to the total weight of the first toluene cut 18. According to one or more embodiments, the first toluene cut 18 is sent to the first column for the distillation of aromatic compounds 4, also referred to as benzene column, and/or to the second column for the distillation of aromatic compounds 5, also referred to as toluene column.

According to one or more embodiments, the incoming feedstock 2 is a hydrocarbon cut containing predominantly (i.e., >50% by weight) molecules, the carbon number of which extends from 6 to 10 carbon atoms. This feedstock can also contain molecules having more than 10 carbon atoms and/or molecules having 5 carbon atoms.

The incoming feedstock 2 of the aromatic complex is rich in aromatics (e.g., >50% by weight) and contains preferably at least 20% by weight of benzene, preferentially at least 30% by weight, very preferably at least 40% by weight, of benzene, with respect to the total weight of the incoming feedstock 2. The incoming feedstock 2 can be produced by catalytic reforming of a naphtha or be a product of a cracking (e.g., steam cracking, catalytic cracking) units or any other means for the production of alkylaromatics.

According to one or more embodiments, the incoming feedstock 2 is at least in part biobased. According to one or more embodiments, the incoming feedstock 2 originates, at least in part, from a process for the conversion of lignocellulosic biomass. For example, an effluent produced by conversion of lignocellulosic biomass can be treated to meet the required specifications of the incoming feedstock 2 as described above, in order to exhibit contents of sulfur-based, nitrogen-based and oxygen-based elements which are compatible with an aromatic complex. According to one or more embodiments, the incoming feedstock 2 comprises less than 10 ppm by weight, preferably less than 5 ppm by weight, very preferably less than 1 ppm by weight, of elemental nitrogen, and/or less than 10 ppm by weight, preferably less than 5 ppm by weight, very preferably less than 1 ppm by weight, of elemental sulfur, and/or less than 100 ppm by weight, preferably less than 50 ppm by weight, very preferably less than 10 ppm by weight, of elemental oxygen.

The top cut 16 from the feedstock separation unit 1, optionally mixed with the bottom product 44 (benzene and toluene) from the stabilization column 12, which will be defined below, is sent to the unit for extraction of the aromatics 3 in order to extract an effluent 19 comprising C6-C7 aliphatic entities, which is exported as co-product from the aromatic complex. The aromatic cut 20 (essentially benzene and toluene), referred to as extract from the unit for extraction of the aromatics 3, optionally mixed with the heavy fraction 21 from the transalkylation unit 8, which will be defined below, is sent to the benzene column 4.

According to one or more embodiments, the aromatic cut 20 is a C6-C7 (e.g., essentially) aromatic hydrocarbon feedstock (A6-A7).

According to one or more embodiments, the fractionation train comprises the columns for the distillation of aromatic compounds 4, 5, 6 and 7, making it possible to separate the following five cuts:

a cut comprising (e.g., essentially) benzene 22;

a cut comprising (e.g., essentially) toluene 23;

a cut comprising (e.g., essentially) xylenes and ethylbenzene 24;

a cut comprising (e.g., essentially) aromatic compounds having 9 and 10 carbon atoms 25;

a cut comprising (e.g., essentially) aromatic compounds, the most volatile entities of which are aromatics having 10 carbon atoms 26.

The benzene column 4 is suitable for: treating the aromatic cut 20, which is a C6-C10 (e.g., essentially) aromatic hydrocarbon feedstock (A6+); producing, at the top, the cut comprising benzene 22, which can be one of the desired products at the outlet of the aromatic complex; and producing, at the bottom, a C7-C10 (e.g., essentially) aromatic effluent 27 (A7+).

The toluene column 5 is suitable for: treating the C7-C10 aromatic effluent 27 (A7+), which is the bottom product from the benzene column 4; producing, at the top, the cut comprising toluene 23, which is sent to the transalkylation unit 8; and producing, at the bottom, a C8-C10 (e.g., essentially) aromatic effluent 28 (A8+).

The third column for the distillation of aromatic compounds 6, also referred to as xylene column, is suitable for: treating the aromatic cut having 8 or more carbon atoms 17 (A8+) of the feedstock of the aromatic complex and optionally the bottom effluent from the toluene column 28; producing, at the top, the cut comprising xylenes and ethylbenzene 24, which is sent to the unit for the separation of the xylenes 10; and producing, at the bottom, an effluent (e.g., essentially) comprising C9-C10 aromatics 29 (A9+).

The fourth column for the distillation of aromatic compounds 7, also referred to as heavy aromatics column, is optional and is suitable for: treating the bottom effluent from the xylene column 29; producing, at the top, the fraction comprising C9-C10 monoaromatics 25; and producing, at the bottom, the cut comprising (e.g., essentially) aromatic compounds, the most volatile entities of which are aromatics having 10 carbon atoms 26 (A10+). Preferably, the bottom cut 26 comprises C11+ compounds.

In the transalkylation unit 8, the fraction comprising C9-C10 monoaromatics 25 (and/or the hydrogenolysis effluent enriched in methyl-substituted aromatic compounds described below) is mixed with the cut comprising toluene 23 originating from the top of the toluene column 5 and feeds the reaction section of the transalkylation unit 8 to produce xylenes by transalkylation of aromatics with a deficit of methyl groups (toluene) and aromatics with an excess of methyl groups (e.g., tri- and tetramethylbenzenes). According to one or more embodiments, the transalkylation unit 8 is fed with benzene (line not represented in the FIGURE), for example when an excess of methyl groups is observed, for the production of para-xylene. According to one or more embodiments, the transalkylation unit 8 directly treats the bottom effluent from the xylene column 29.

According to one or more embodiments, the transalkylation unit 8 comprises at least one first transalkylation reactor suitable for being used under at least one of the following operating conditions:

temperature of between 200° C. and 600° C., preferentially of between 350° C. and 550° C., and more preferentially still of between 380° C. and 500° C.;

pressure of between 2 and 10 MPa, preferentially of between 2 and 6 MPa and more preferentially of between 2 and 4 MPa;

WWH (ratio of the flow rate of feedstock to the weight of catalyst) of between 0.5 and 5 $h^{-1}$, preferentially of between 1 and 4 $h^{-1}$ and more preferentially of between 2 and 3 $h^{-1}$.

According to one or more embodiments, the first transalkylation reactor is operated in the presence of a catalyst comprising zeolite, for example ZSM-5. According to one or more embodiments, the second transalkylation reactor is of fixed bed type.

According to one or more embodiments, the effluents from the reaction section of the transalkylation unit 8 are separated in a first separation column (not represented) downstream of said reaction section of the transalkylation unit 8. A cut comprising at least a part of the benzene, and the more volatile entities, 38 (C6-) is extracted at the top of the first separation column and is sent to an optional stabilization column 12, making it possible in particular to remove the more volatile entities (e.g., C5-) from the aromatic complex. The heavy fraction of the effluents from the first separation column comprising (e.g., essentially) aromatics having at least 7 carbon atoms 21 (A7+) is optionally recycled to the fractionation train 4-7, for example to the benzene column 4.

The cut comprising xylenes and ethylbenzene 24 is treated in the unit for the separation of the xylenes 10 to produce a fraction or an extract 39, comprising para-xylene, and a raffinate 40. The extract 39 can be subsequently distilled (e.g., if separation by adsorption SMB), for example by means of an extract column and then of an additional toluene column (which are not shown) in the case where toluene is used as desorbent, in order to obtain high-purity para-xylene exported as main product. The raffinate 40 from the unit for the separation of the xylenes 10 comprises (e.g., essentially) ortho-xylene, meta-xylene and ethylbenzene and feeds the isomerization unit 11.

According to one or more embodiments, the unit for the separation of the xylenes 10 also separates a second toluene cut 41 comprising at least 90% by weight, preferably at least 95% by weight, very preferably at least 99% by weight, of toluene, with respect to the total weight of the second toluene cut 41. The toluene cut 41 can, for example, be a part of the toluene used as desorbent when the unit for the separation of the xylenes 10 comprises a "simulated moving bed" adsorption unit. According to one or more embodiments, the second toluene cut 41 is sent to the transalkylation unit 8.

In the isomerization reaction section (not represented) of the isomerization unit 11, the isomers of the para-xylene are isomerized, whereas the ethylbenzene can be: isomerized to give a mixture of C8 aromatics, for example if it is desired to produce mainly para-xylene; and/or dealkylated to produce benzene, for example if it is desired to produce both para-xylene and benzene. According to one or more embodiments, the effluents from the isomerization reaction section are sent to a second separation column (not represented) to produce, at the bottom, an isomerate 42 enriched in para-xylene, which is preferably recycled to the xylene column 6; and to produce, at the top, a hydrocarbon cut comprising compounds having 7 or less carbon atoms 43 (C7-) which is sent to the optional stabilization column 12, for example with the cut comprising at least a part of the benzene, and the more volatile entities, 38.

According to one or more embodiments, the isomerization unit 11 comprises a first isomerization zone working in the liquid phase and/or a second isomerization zone working in the gas phase, as is described in the patents listed above. According to one or more embodiments, the isomerization unit 11 comprises a first isomerization zone working in the liquid phase and a second isomerization zone working in the gas phase. According to one or more embodiments, a first part of the raffinate 40 is sent to the liquid-phase isomerization unit, in order to obtain a first isomerate feeding directly and at least in part the separation unit 10 and a second part of the raffinate 40 is sent to the gas-phase isomerization unit, in order to obtain an isomerate which is sent to the xylene column 6.

According to one or more embodiments, the gas-phase isomerization zone is suitable for being used under at least one of the following operating conditions:

temperature of greater than 300° C., preferably from 350° C. to 480° C.;

pressure of less than 4.0 MPa, and preferably from 0.5 to 2.0 MPa;

hourly space velocity of less than 10 $h^{-1}$ (10 litres per litre per hour), preferably between 0.5 $h^{-1}$ and 6 $h^{-1}$;

hydrogen to hydrocarbon molar ratio of less than 10, and preferably of between 3 and 6;

in the presence of a catalyst comprising at least one zeolite exhibiting channels, the opening of which is defined by a ring having 10 or 12 oxygen atoms (10 MR or 12 MR), and at least one metal from group VIII with a content of between 0.1% and 0.3% by weight (reduced form), limits included, with respect to the total weight of the catalyst.

According to one or more embodiments, the liquid-phase isomerization zone is suitable for being used under at least one of the following operating conditions:

temperature of less than 300° C., preferably 200° C. to 260° C.;

pressure of less than 4 MPa, preferably 2 to 3 MPa;

hourly space velocity (HSV) of less than 10 $h^{-1}$ (10 litres per litre per hour), preferably of between 2 and 4 $h^{-1}$;

in the presence of a catalyst comprising at least one zeolite exhibiting channels, the opening of which is defined by a ring having 10 or 12 oxygen atoms (10 MR or 12 MR), preferentially a catalyst comprising at least one zeolite exhibiting channels, the opening of which is defined by a ring having 10 oxygen atoms (10 MR), and more preferably still a catalyst comprising a zeolite of ZSM-5 type.

The term HSV corresponds to the volume of hydrocarbon feedstock injected hourly, with respect to the volume of catalyst charged.

According to one or more embodiments, the optional stabilization column 12 produces: at the bottom, a stabilized cut comprising (e.g., essentially) benzene and toluene 44, which is optionally recycled at the inlet of the feedstock separation unit 1 and/or of the unit for extraction of the aromatics 3; and, at the top, a cut of more volatile entities 45 (e.g., C5-), which is removed from the aromatic complex.

According to one or more embodiments, the selective hydrogenolysis unit 9 is suitable for:

treating the monoaromatics having between 9 and 10 carbon atoms 25; and producing a hydrogenolysis effluent enriched in methyl-substituted aromatic compounds 46. Specifically, the selective hydrogenolysis unit 9 can be suitable for treating the aromatics having between 9 and 10 carbon atoms 25 by converting one or more alkyl groups having at least two carbon atoms (ethyl, propyl, butyl, isopropyl, and the like, groups) attached to a benzene ring into one or more methyl groups, that is to say groups formed of a single $CH_3$ group. The major advantage of the selective hydrogenolysis unit 9 is that of increasing the content of $CH_3$ groups and lowering the content of ethyl, propyl, butyl, isopropyl, and the like, groups in the feedstock of the isomerization unit 11, in order to increase the rate of production of xylenes, and in particular of para-xylene, in said isomerization unit 11.

According to one or more embodiments, the selective hydrogenolysis unit 9 comprises at least one hydrogenolysis reactor suitable for being used under at least one of the following operating conditions:

temperature of between 300° C. and 550° C., preferentially of between 350° C. and 500° C. and more preferentially still of between 370° C. and 450° C.;

pressure of between 0.1 and 3 MPa, preferentially of between 0.2 and 2 MPa and more preferentially of between 0.2 and 1 MPa;

$H_2$/HC (hydrocarbon feedstock) molar ratio of between 1 and 10 and preferentially of between 1.5 and 6;

WWH of between 0.1 and 50 $h^{-1}$ (e.g., 0.5-50 $h^{-1}$), preferentially of between 0.5 and 30 $h^{-1}$ (e.g., 1-30 $h^{-1}$) and more preferentially of between 1 and 20 $h^{-1}$ (e.g., 2-20 $h^{-1}$, 5-20 $h^{-1}$).

According to one or more embodiments, the hydrogenolysis reactor is operated in the presence of a catalyst comprising at least one metal from group VIII of the Periodic Table, preferably nickel and/or cobalt, deposited on a porous support comprising at least one crystalline or noncrystalline refractory oxide having structured or unstructured porosity. According to one or more embodiments, the metal from group VIII is nickel. The presence of a promoter (group VIb, VIIb, VIII, Ib or IIb) is also possible. The catalyst is supported on a refractory oxide (e.g., alumina or silica), optionally treated with a base in order to neutralize it.

According to one or more embodiments, the hydrogenolysis reactor is of fixed bed type and the catalyst support is provided in the form of extrudates. According to one or more embodiments, the hydrogenolysis reactor is of moving bed type and the catalyst support is provided in the form of approximately spherical beads. A moving bed can be defined as being a gravity flow bed, such as those encountered in the catalytic reforming of petroleums.

In the pyrolysis unit 13, biomasse 30 is in particular converted, at least partially, into a pyrolysis effluent 31 comprising hydrocarbon compounds, the carbon number of which extends from 6 to 10 carbon atoms. The pyrolysis effluent 31 feeds the incoming feedstock 2 of the aromatic complex. The pyrolysis unit 13 also produces a pyrolysis gas 32 comprising CO and $H_2$, and a line of middle distillates 33.

According to one or more embodiments, the pyrolysis effluent 31 feeds the optional hydrotreating unit before feeding the incoming feedstock 2 of the aromatic complex. Advantageously, the optional hydrotreating unit makes it possible to reduce the content of oxygen-based compounds of the pyrolysis effluent 31 to the specifications required by the incoming feedstock 2 of the aromatic complex.

According to one or more embodiments, the biomass 30 is a lignocellulosic biomass or one or more constituents of lignocellulosic biomass chosen from the group formed by cellulose, hemicellulose and/or lignin. According to one or more embodiments, lignocellulosic biomass comprises at least the following compounds: wood, agricultural waste, vegetable waste, farm residues (straw, maize stovers, and the like), forestry residues (products from first thinning), forestry products, dedicated crops (short-rotation coppice), residues from the food processing industry, organic household wastes, wastes from woodworking plants, waste wood from the building industry, recycled or non-recycled paper, by-products of the papermaking industry (Kraft lignin, black liquors resulting from the manufacture of paper pulp, and the like).

According to one or more embodiments, the biomass is sent to at least one pretreatment unit (not represented) before it is introduced into the pyrolysis unit 13. Preferably, the biomass is ground and dried until a target particle size distribution is obtained. A feedstock exhibiting a particle diameter of between 0.3 and 0.5 mm can advantageously be obtained. Typically, the size of the particles of the lignocellulosic biomass to be pyrolysed is a particle size sufficient to pass through a 1 mm sieve up to a particle size sufficient to pass through a 30 mm sieve.

According to one or more embodiments, the optionally pretreated biomass is charged to a pneumatic entrainment or transportation compartment so as to be entrained into the pyrolysis unit 13 by an entraining fluid. Preferably, the entraining fluid used is gaseous nitrogen. However, it is also envisaged that other non-oxidizing entraining fluids can be used. Preferably, the pyrolysis gas 32 produced during the process can be in part recycled and used as entraining fluid. In this way, the cost of carrying out the pyrolysis can be greatly reduced. The biomass can be charged to a feed hopper or another device which makes it possible to convey the biomass into the entrainment compartment in an appropriate amount. In this way, a constant amount of biomass is delivered to the entrainment compartment.

According to one or more embodiments, the entraining fluid advantageously transports the biomass from the entrainment compartment into the pyrolysis unit 13 through a feed tube. Preferably, the feed tube is cooled in order to keep the temperature of the biomass at a required level before it enters the pyrolysis unit 13. The feed tube can be cooled by jacketing the tube, typically with an air-cooled or liquid-cooled jacket. However, it is also envisaged for the feed tube not to be cooled.

According to one or more embodiments, the pyrolysis unit 13 comprises at least one pyrolysis reactor suitable for functioning as fluid bed or fixed bed. According to one or more embodiments, the pyrolysis unit 13 comprises at least one pyrolysis reactor suitable for functioning as fluid bed. According to one or more embodiments, the pyrolysis unit 13 comprises at least one pyrolysis reactor suitable for functioning as fluid bed. According to one or more embodiments, the pyrolysis reactor is suitable for being used under at least one of the following operating conditions:

presence of a catalyst, preferably a zeolite catalyst, preferably a zeolite catalyst comprising at least one zeolite chosen from ZSM-5, ferrierite, zeolite beta, zeolite Y, mordenite, ZSM-23, ZSM-57, EU-1 or ZSM-11, preferably a catalyst comprising only a zeolite of ZSM-5 type; the zeolite used in the catalyst can advantageously be doped with a metal chosen from iron, gallium, zinc and lanthanum;

a temperature of between 400° C. and 1000° C., preferably between 400° C. and 650° C., in a preferred way between 450° C. and 600° C. and in a very preferred way between 450° C. and 590° C.;

an absolute pressure of between 0.1 and 0.5 MPa;

an HSV of between 0.01 and 10 h$^{-1}$, preferably between 0.01 and 5 h$^{-1}$, in a preferred way between 0.1 and 3 h$^{-1}$ and in a very preferred way between 0.1 and 3 h$^{-1}$ (the HSV is the ratio of the flow rate by volume of feedstock to the volume of catalyst used).

According to one or more embodiments, the biomass undergoes, in the reactor, a rapid pyrolysis on coming into contact with the hot catalyst originating from a regenerator, which in this stage acts as heat carrier. The gases resulting from this pyrolysis will subsequently react over the catalyst, which this time performs its role of catalyst making it possible to catalyse the reactions producing the desired chemical intermediates.

The products obtained on conclusion of the catalytic pyrolysis stage are advantageously recovered in the form of a pyrolysis gas mixture comprising, at least in part, BTX (Benzene, Toluene, Xylenes). Said gas mixture is subsequently advantageously sent to a fractionation section, so as to separate at least the following cuts:

the pyrolysis effluent 31,
the pyrolysis gas 32,
middle distillates 33; and
water (not represented).

According to one or more embodiments, the coked catalyst and the unconverted biomass, usually denoted "char", are advantageously withdrawn from the reactor and preferably sent to a stripper so as to remove the hydrocarbons potentially adsorbed, and thus to prevent their combustion in the regenerator, this being achieved by bringing into contact with a gas chosen from steam, an inert gas, such as, for example, nitrogen, and optionally a part of the pyrolysis gas 32. Said coked catalyst and the char, which are optionally stripped, are advantageously sent to a regenerator where coke and char are incinerated by addition of air or of oxygen. The catalyst, thus regenerated, is advantageously recycled in the reactor of the catalytic pyrolysis stage in order to undergo another cycle. The catalytic pyrolysis stage of the process according to the invention makes possible the production of at least 10% by weight and preferably of at least 15% by weight of aromatics, with respect to the total weight of the reaction products obtained, with a selectivity of at least 65% and preferably of at least 70% for BTX. The process also makes it possible to obtain, in addition to the pyrolysis effluent 31 and the pyrolysis gas 32, a heavier liquid fraction, which is predominantly aromatic, referred to as middle distillates, 33, which can advantageously be upgraded in a process external to the process according to the invention.

According to one or more embodiments, a part of the pyrolysis gas 32 is recycled, preferably via a compressor, in the reactor of the catalytic pyrolysis stage. This gas stream then serves as fluid for entrainment of the feedstock into said reactor. In this case, a purge of said gaseous recycle effluent is unavoidable and is preferably carried out either upstream or downstream of said compressor.

According to one or more embodiments, the pyrolysis effluent 31 is a hydrocarbon cut containing predominantly (i.e., >50% by weight) molecules, the carbon number of which extends from 6 to 10 carbon atoms. This pyrolysis effluent 31 can also contain molecules having more than 10 carbon atoms and/or molecules having 5 carbon atoms. The pyrolysis effluent 31 is rich in aromatics (e.g. >50% by weight, preferably at least 65% by weight, very preferably at least 75% by weight), contains, at least in part, BTX and contains preferably at least 20% by weight of benzene, preferentially at least 30% by weight, very preferably at least 40% by weight of benzene, with respect to the total weight of the pyrolysis effluent 31. According to one or more embodiments, the pyrolysis effluent 31 is treated to meet the required specifications of the incoming feedstock 2 as described above, in order to exhibit contents of sulfur-based, nitrogen-based and oxygen-based elements which are compatible with an aromatic complex. According to one or more embodiments, the incoming feedstock 2 comprises less than 10 ppm by weight, preferably less than 5 ppm by weight, very preferably less than 1 ppm by weight, of elemental nitrogen, and/or less than 10 ppm by weight, preferably less than 5 ppm by weight, very preferably less than 1 ppm by weight, of elemental sulfur, and/or less than 100 ppm by weight, preferably less than 50 ppm by weight, very preferably less than 10 ppm by weight, of elemental oxygen.

According to one or more embodiments, the feedstock 2 of the aromatic complex comprises at least 60% by weight, preferably at least 80% by weight, very preferably at least 90% by weight, such as at least 95% by weight, of pyrolysis effluent 31, with respect to the total weight of the feedstock.

According to one or more embodiments, the pyrolysis gas 32 produced by the pyrolysis unit 13 consists of a mixture containing predominantly (e.g., comprising at least 50% by weight) hydrogen, CO and $CO_2$. According to one or more embodiments, the pyrolysis gas 32 comprises at least 20% by weight of CO, preferably at least 30% by weight of CO, very preferably at least 40% by weight of CO (e.g., at least 50% by weight of CO), with respect to the total weight of the pyrolysis gas 32. According to one or more embodiments, the pyrolysis gas 32 comprises at least 0.2% by weight of $H_2$, preferably at least 0.5% by weight of $H_2$, very preferably at least 0.8% by weight of $H_2$, with respect to the total weight of the pyrolysis gas 32. According to one or more embodiments, the pyrolysis gas 32, at the outlet of the pyrolysis unit 13, contains approximately 30% (e.g., ±10% by weight) by weight of $CO_2$, with respect to the total weight of the pyrolysis gas 32. According to one or more embodiments, the pyrolysis gas 32 additionally comprises alkanes comprising from 1 to 3 carbon atoms and light olefins comprising from 2 to 4 carbon atoms. According to one or more embodiments, the pyrolysis gas 32 contains ethylene and propylene (e.g., less than 10% by weight) and also water (e.g., less than 3% by weight).

According to one or more embodiments, it is not necessary to treat the pyrolysis gas 32 in a dedicated unit. The pyrolysis gas can be sent directly to the Fischer-Tropsch reaction section 14. Thus, the aromatics produced will retain their biobased nature. According to one or more embodiments, the pyrolysis gas 32 can be purified before being converted into a mixture of hydrocarbons in the Fischer-Tropsch reaction section 14. According to one or more embodiments, the pyrolysis gas 32 is treated in order to reduce its content of sulfur-based compounds, nitrogen-based compounds, halogens, heavy metals and transition metals. The main technologies for the purification of synthesis gases are: adsorption, absorption, catalytic reactions. These different purification methods are well known to a person skilled in the art; reference may be made, for example, to: Oil & Gas Science and Technology—Rev. IFP Energies nouvelles, Vol. 68 (2013), No. 4, or to Applied Energy, 237 (2019), 227-240.

According to one or more embodiments, the optional unit for the separation of $CO_2$ which is positioned between the pyrolysis unit 13 and the Fischer-Tropsch reaction section 14 is suitable for extracting, at least in part, the $CO_2$ from the pyrolysis gas 32 at the outlet of the pyrolysis unit 13, so that the pyrolysis gas 32 at the inlet of the Fischer-Tropsch synthesis reactor 14 comprises less than 10% by weight of $CO_2$, preferably less than 5% by weight of $CO_2$, very preferably less than 2% by weight of $CO_2$. For example, at the outlet of the pyrolysis unit 13, the inert $CO_2$ gas can be removed by a stage of removal of acid gases, carried out, for example, using systems for absorption by solvents, or by means of membranes. The acid gases are composed generally of $H_2S$, COS and $CO_2$. Current processes for the removal of said acid gases generally involve a countercurrentwise absorption with a regenerator solvent, in an absorbent column. According to one or more embodiments, the optional unit for separation of the $CO_2$ is positioned upstream of the optional backup line 34 providing the contribution of hydrogen.

According to one or more embodiments, the middle distillates 33 comprise compounds exhibiting a number of carbon atoms of greater than or equal to 9. According to one or more embodiments, the middle distillates 33 comprise at least 50% by weight of C9+ compounds. The C9+ compounds mainly (e.g., at least 50% by weight) consist of di- and triaromatics which are optionally alkylated. The middle distillates 33 can be upgraded directly as bunker fuel, for example, or can undergo a hydrotreating and/or hydrocracking in order to improve their properties and to upgrade them as jet fuel or as diesel oil.

According to one or more embodiments, a contribution of $H_2$ fed by the optional backup line 34 is added to the pyrolysis gas 32 so that the $H_2/CO$ molar ratio of the pyrolysis gas 32 at the inlet of the Fischer-Tropsch reaction section 14 is between 0.5 and 2, preferably between 0.6 and 1.

In the Fischer-Tropsch reaction section 14, the pyrolysis gas 32 is in particular converted, at least partially, into a synthesis effluent 35 comprising hydrocarbon compounds, the carbon number of which extends from 3 to 22 carbon atoms. The synthesis effluent 35 feeds, at least partially, the pyrolysis unit 13.

According to one or more embodiments, the Fischer-Tropsch reaction section 14 is suitable for being operated under at least one of the following operating conditions:
   temperature of between 250° C. and 400° C., preferably of between 300° C. and 350° C. and very preferably still of between 300° C. and 340° C.;
   pressure of between 1 and 5 MPa, preferably of between 1.5 and 4 MPa and very preferably of between 2 and 3 MPa (e.g. at 2.5 MPa±2);
   catalyst comprising iron as active phase;
   flow rate by volume of the synthesis effluent 35 of between 0.2 and 3 $l/g_{cata}/h$ and preferably between 0.5 and 1.5 $l/g_{cata}/h$.

According to one or more embodiments, the catalyst of the Fischer-Tropsch reaction section 14 is prepared by (co)precipitation or (co)impregnation. According to one or more embodiments, the catalyst of the Fischer-Tropsch reaction section 14 comprises between 70% and 90% by weight of $Fe_2O_3$, between 1% and 5% by weight of CuP, between 1% and 5% by weight of $K_2O$, between 0.01% and 0.1% by weight of $Na_2O$ and between 10% and 20% by weight of alumina and/or of silica and/or of zeolite (silicalite), with respect to the total weight of the catalyst. For example, the catalyst can comprise 78.4% by weight of $Fe_2O_3$, 3.4% by weight of CuP, 2.6% by weight of $K_2O$, 0.04% by weight of $Na_2O$ and 15% by weight of $SiO_2$.

According to one or more embodiments, the Fischer-Tropsch reaction section 14 is suitable for functioning as fluid bed, fixed bed, or as slurry (e.g., catalyst kept in suspension in a liquid medium consisting of the products of the reaction; the stirring of this reaction medium results from the injection of the synthesis gas within the liquid phase), the fluid bed technology being the preferred embodiment. These different reactor technologies are well known to a person skilled in the art; reference may be made to: International Journal of Chemical Reactor Engineering, 2014, 12(1): 1-26. The method of manufacture of the catalyst depends on the mode of operation of the Fischer-Tropsch reaction section 14. For an implementation as fluid bed, the catalysts are preferably attrition-resistant. For example, the catalysts based on fused iron, prepared by melting, meet this requirement.

According to one or more embodiments, the synthesis effluent 35 comprises a mixture of hydrocarbons which are liquid at ambient temperature. According to one or more embodiments, the synthesis effluent 35 comprises a mixture comprising C3 to C22 olefins, for example at a content of at least 50% by weight, with respect to the total weight of the synthesis effluent 35. According to one or more embodiments, the content by weight of C3 to C22 olefins is at least 60% by weight and preferably at least 70% by weight, with respect to the total weight of the synthesis effluent 35. According to one or more embodiments, the synthesis effluent 35 additionally comprises C3 to C22 paraffins, for example at a content of between 20% and 35% by weight, and optionally oxygen-based compounds, for example at a content of between 1% and 5% by weight, with respect to the total weight of the synthesis effluent 35. According to one or more embodiments, the synthesis effluent 35 additionally comprises aromatic compounds, for example at a content of between 1% and 10% by weight, with respect to the total weight of the synthesis effluent 35. According to one or more embodiments, the synthesis effluent 35 is recycled in its entirety in the pyrolysis unit 13.

Thus, the combination of a Fischer-Tropsch reaction section 14 and the recycle of the synthesis effluent 35 to the pyrolysis unit 13 makes it possible to produce additional aromatics from the CO which is a by-product of the pyrolysis unit 13.

The device and the process according to the invention thus make it possible to obtain gains ranging up to 30% by weight in aromatic compounds, the gain being predominantly a gain of para-xylene (of the order of 50% by weight), the amount of benzene remaining substantially unchanged.

In the present patent application, the groups of chemical elements are given, by default, according to the CAS classification (CRC Handbook of Chemistry and Physics, published by CRC Press, Editor-in-Chief D. R. Lide, 81st edition, 2000-2001). For example, group VIII according to the CAS classification corresponds to the metals from columns 8, 9 and 10 according to the new IUPAC classification; group VIb according to the CAS classification corresponds to the metals from column 6 according to the new IUPAC classification.

EXAMPLES

Example of Reference Device

Use is made of an example of reference device for the conversion of a feedstock comprising a mixture of aromatic compounds resulting from a process for the conversion of the lignocellulosic biomass based on a conversion by catalytic pyrolysis.

The example of reference device is similar to the device represented in the FIGURE, except that the transalkylation unit 8 is replaced by a disproportionation unit (not represented). A disproportionation reaction is called a transalkylation reaction when the feedstock does not comprise heavy aromatics (e.g., A9 and A10). In a transalkylation reactor, disproportionation reactions of toluene also occur. All this is well known to a person skilled in the art.

Furthermore, the example of reference device does not employ the following units:
heavy aromatics column 7;
selective hydrogenolysis unit 9;
stabilization column 12;
Fischer-Tropsch reaction section 14.

The flow rates of said aromatic compounds of the feedstock to be treated, at the inlet of the feedstock separation unit 1, are as follows:
benzene: 2.63 t/h;
toluene: 5.64 t/h;
ethylbenzene: 0.15 t/h; and
xylenes: 3.56 t/h.
i.e., a total of 11.98 t/h of aromatic compounds.

Furthermore, the pyrolysis unit 13 produces CO, which is not converted into other chemical compounds. The flow rate of CO produced is 22.25 t/h.

In the reference device, all of the toluene is converted, by a disproportionation unit, into benzene and xylenes. The xylenes of the feedstock and those produced by disproportionation are isomerized to give para-xylene, which is separated from the xylenes mixture at thermodynamic equilibrium at the outlet of the isomerization unit, by means of a simulated moving bed adsorption unit. This set of unit operations makes it possible, in the best of cases (assuming a selectivity of 100% for each unit operation), to produce the following compounds:
benzene: 5.02 t/h;
para-xylene: 6.96 t/h
aromatic total: 11.98 t/h.

Example of Device According to the Invention

The example of device according to the invention makes it possible to increase the total amount of aromatics produced for the same flow rate of biomass feedstock entering the catalytic pyrolysis as in the reference device, and in particular to increase the amount of para-xylene produced.

The example of device according to the invention is similar to the device represented in the FIGURE but does not employ the following optional units:
heavy aromatics column 7;
selective hydrogenolysis unit 9;
stabilization column 12.

In comparison with the reference device scheme, the unit for the separation of $CO_2$ at the outlet of the pyrolysis unit 13, as well as the Fischer-Tropsch synthesis reaction section 14, which treats all of the CO, namely 22.25 t/h, are added in particular.

All of the effluent from the Fischer-Tropsch synthesis reaction section 14, effluent containing unconverted CO, $CO_2$, paraffins, olefins, oxygen-based compounds and water, is recycled at the inlet of the pyrolysis unit 13.

Thus, the recycle resulting from the Fischer-Tropsch synthesis 14 is converted in the same pyrolysis unit 13 as the lignocellulosic biomass.

According to the example of device according to the invention, and with the same amount of lignocellulosic biomass at the inlet of the catalytic pyrolysis unit 13 and the same yields of the unit operations as in the example of reference device, the following performances, compared with those of the reference device, are obtained in Table 1.

The pyrolysis gas 32 containing in particular CO, $CO_2$ and hydrogen is purified by the techniques well known to a person skilled in the art, so as to recover a synthesis gas consisting of a mixture of CO and of hydrogen in $H_2/CO$ proportions of 0.6 by moles. This synthesis gas is converted in the Fischer-Tropsch synthesis reaction section 14 operated at a temperature of between 300° C. and 350° C., at a pressure substantially equal to 2.5 MPa and in the presence of an iron-based catalyst. The flow rate of CO, the feedstock of the Fischer-Tropsch reaction section, is 22.25 t/h (22 250 kg/h). The conversion of the CO is then 85%.

At the outlet of the Fischer-Tropsch reaction section, an effluent predominantly composed of unconverted CO (3337.5 kg/h), of $CO_2$ (14 859.9 kg/h) and of an effluent of hydrocarbons (4728 kg/h) is obtained. The effluent composed of hydrocarbons contains 58.94% by weight of olefins, 29.4% by weight of paraffins, 3.74% by weight of aromatic compounds and 7.92% by weight of oxygen-based compounds.

All of the effluent is recycled at the inlet of the unit for pyrolysis 13 of the biomass in order to be converted therein.

TABLE 1

|  | Example of reference device | Example of device according to the invention |
|---|---|---|
| CO at the outlet pyrolysis unit (t/h) | 22.25 | 22.25 |
| $H_2$ at the outlet pyrolysis unit (t/h) | 0.338 | 0.532 |
| $CO_2$ at the outlet pyrolysis unit (t/h) | 15.99 | 30.84 |
| CO at the outlet of the complex | 22.25 | 3.34 |
| Feedstock (t/h) of the aromatic complex | | |
| Benzene | 2.63 | 2.78 |
| Toluene | 5.64 | 6.14 |
| Ethylbenzene | 0.15 | 0.28 |
| Xylenes | 3.56 | 4.66 |
| A9 + A10 Aromatics | 0 | 1.55 |
| Total of the aromatics | 11.98 | 15.41 |
| Products (t/h) | | |
| Benzene | 5.02 | 4.683 |
| p-Xylene | 6.96 | 10.727 |
| Total aromatics | 11.98 | 15.41 |

Table 1 shows that the implementation according to the invention makes it possible to produce 29% by weight more of aromatics (15.41 t/h instead of 11.98 t/h). This increase in aromatic compounds concerns essentially the para-xylene, which changes from 6.96 t/h to 10.727 t/h, i.e. a gain of 54%.

The invention claimed is:
1. A conversion device for the conversion of a feedstock of aromatic compounds, comprising:
a fractionation train suitable for extracting at least one cut comprising benzene, one cut comprising toluene and one cut comprising xylenes and ethylbenzene from the feedstock
a unit for the separation of the xylenes suitable for treating the cut comprising xylenes and ethylbenzene and producing an extract comprising para-xylene and a raffinate comprising ortho-xylene, meta-xylene and ethylbenzene;
an isomerization unit suitable for treating the raffinate and producing an isomerate enriched in para-xylene which is sent to the fractionation train;
a pyrolysis unit suitable for treating biomass, producing at least one pyrolysis effluent comprising hydrocarbon compounds of 6 to 10 carbon atoms and feeding at least partially the at least one pyrolysis effluent to the feedstock, and producing a pyrolysis gas comprising at least CO and $H_2$; and a Fischer-Tropsch synthesis reaction section suitable for treating the pyrolysis gas at least in part, producing a synthesis effluent comprising hydrocarbon compounds of 3 to 22 carbon atoms, and sending the synthesis effluent, at least in part, to the pyrolysis unit.

2. The conversion device according to claim 1, in which the pyrolysis gas additionally comprises $CO_2$ at the outlet of the pyrolysis unit.

3. The conversion device according to claim 2, additionally comprising a unit for the separation of $CO_2$ positioned between the pyrolysis unit and the Fischer-Tropsch reaction section, and suitable for extracting, at least in part, $CO_2$ from the pyrolysis gas.

4. The conversion device according to claim 1, in which the fractionation train is suitable for extracting a C9-C10 monoaromatics cut from the feedstock.

5. The conversion device according to claim 4, additionally comprising a transalkylation unit suitable for treating the C9-C10 monoaromatics cut with the toluene-comprising cut and producing xylenes which are sent to the fractionation train.

6. The conversion device according to claim 5, additionally comprising a selective hydrogenolysis unit suitable for:
   treating the C9-C10 monoaromatics cut; and
   producing a hydrogenolysis effluent enriched in methyl-substituted aromatic compounds which is sent to the transalkylation unit.

7. The conversion device according to claim 1, in which the Fischer-Tropsch synthesis reaction section is suitable for recycling the synthesis effluent in its entirety in the pyrolysis unit.

8. A conversion process for the conversion of a feedstock of aromatic compounds, comprising the following stages:
   fractionating the feedstock in a fractionation train in order to extract at least one benzene-comprising cut, one toluene-comprising cut and one cut comprising xylenes and ethylbenzene
   separating the cut comprising xylenes and ethylbenzene in a unit for the separation of the xylenes and producing an extract comprising para-xylene and a raffinate comprising ortho-xylene, meta-xylene and ethylbenzene;
   isomerizing the raffinate in an isomerization unit and producing an isomerate enriched in para-xylene;
   sending the isomerate enriched in para-xylene to the fractionation train;
   treating biomass in a pyrolysis unit in order to produce at least one pyrolysis effluent comprising hydrocarbon compounds of 6 to 10 carbon atoms and feeding, at least partially, the at least one pyrolysis effluent to the feedstock, and to produce a pyrolysis gas comprising at least CO and $H_2$;
   treating, at least in part, the pyrolysis gas in a Fischer-Tropsch synthesis reaction section in order to produce a synthesis effluent comprising hydrocarbon compounds of 3 to 22 carbon atoms; and
   sending the synthesis effluent, least in part, to the pyrolysis unit.

9. The conversion process according to claim 8, in which the pyrolysis unit comprises at least one reactor used under the following operating conditions:
   presence of a catalyst, optionally the catalyst is a zeolite catalyst comprising at least one zeolite chosen from ZSM-5, ferrierite, zeolite beta, zeolite Y, mordenite, ZSM-23, ZSM-57, EU-1 or ZSM-11; the catalyst optionally doped with a metal chosen from iron, gallium, zinc and lanthanum;
   a temperature of between 400° C. and 1000° C.;
   an absolute pressure of between 0.1 and 0.5 MPa; and
   an HSV of between 0.01 and 10 $h^{-1}$.

10. The conversion process according to claim 8, in which the Fischer-Tropsch synthesis reaction section is used under the following operating conditions:
    a temperature of between 250° C. and 400° C.,
    a pressure of between 1 and 5 MPa,
    a catalyst comprising iron as active phase; and
    a flow rate by volume of the synthesis effluent of between 0.2 and 3.1 $l/g_{cata}/h$.

11. The conversion process according to claim 8, in which the isomerization unit comprises a gas-phase isomerization zone and/or a liquid-phase isomerization zone,
    in which the gas-phase isomerization zone is used under the following operating conditions:
    temperature of greater than 300° C.;
    pressure of less than 4.0 MPa;
    hourly space velocity of less than 10 $h^{-1}$;
    hydrogen to hydrocarbon molar ratio of less than 10;
    in the presence of a catalyst comprising at least one zeolite exhibiting channels, the opening of which is defined by a ring having 10 or 12 oxygen atoms, and at least one metal from group VIII with a content of between 0.1% and 0.3% by weight, limits included, and in which the liquid-phase isomerization zone is used under the following operating conditions:
    temperature of less than 300° C.;
    pressure of less than 4 MPa;
    hourly space velocity of less than 10 $h^{-1}$;
    in the presence of a catalyst comprising at least one zeolite exhibiting channels, the opening of which is defined by a ring having 10 or 12 oxygen atoms.

12. The conversion process according to claim 8, in which the transalkylation unit comprises at least one first transalkylation reactor used under the following operating conditions:
    temperature of between 200° C. and 600° C.;
    pressure of between 2 and 10 MPa;
    WWH of between 0.5 and 5 $h^{-1}$.

13. The conversion process according to claim 8, in which the pyrolysis gas additionally comprises $CO_2$ at the outlet of the pyrolysis unit.

14. The conversion process according to claim 13, comprising the following stage:
    extracting, at least in part, the $CO_2$ from the pyrolysis gas in a unit for the separation of $CO_2$ positioned between the pyrolysis unit and the Fischer-Tropsch reaction section.

15. The conversion process according to claim 8, in which the synthesis effluent is recycled in its entirety in the pyrolysis unit.

* * * * *